US 011571122B2

(12) United States Patent
Murase et al.

(10) Patent No.: US 11,571,122 B2
(45) Date of Patent: Feb. 7, 2023

(54) OPHTHALMOLOGIC IMAGE PROCESSING METHOD AND FUNDUS IMAGING APPARATUS

(71) Applicant: NIDEK CO., LTD., Aichi (JP)

(72) Inventors: Yuji Murase, Aichi (JP); Naoto Honda, Aichi (JP)

(73) Assignee: NIDEK CO., LTD., Aichi (JP)

( * ) Notice: Subject to any disclaimer, the term of this patent is extended or adjusted under 35 U.S.C. 154(b) by 636 days.

(21) Appl. No.: 16/585,117

(22) Filed: Sep. 27, 2019

(65) Prior Publication Data

US 2020/0100672 A1    Apr. 2, 2020

(30) Foreign Application Priority Data

Sep. 28, 2018  (JP) .............................. JP2018-185472

(51) Int. Cl.
*A61B 3/12*    (2006.01)
*A61B 3/00*    (2006.01)
(Continued)

(52) U.S. Cl.
CPC .............. *A61B 3/12* (2013.01); *A61B 3/0025* (2013.01); *G06T 5/40* (2013.01); *G06T 7/44* (2017.01);
(Continued)

(58) Field of Classification Search
CPC .......... A61B 3/12; A61B 3/0025; H04N 1/60; H04N 1/6027; H04N 1/6033;
(Continued)

(56) References Cited

U.S. PATENT DOCUMENTS 8,022,964 B2 * 9/2011 Pettigrew ................. G09G 5/06
715/848
9,204,790 B2 * 12/2015 Wada ....................... A61B 3/12
(Continued)

FOREIGN PATENT DOCUMENTS

JP    2007-513703 A    5/2007
JP    2009-219644 A   10/2009
(Continued)

OTHER PUBLICATIONS

Office Action dated Sep. 6, 2022, issued by the Japan Patent Office in counterpart Japanese Patent Application No. 2018-185472.

*Primary Examiner* — Wesner Sajous
(74) *Attorney, Agent, or Firm* — Sughrue Mion, PLLC

(57) ABSTRACT

An image processor performs a histogram acquisition step of acquiring a histogram representing a distribution of gradation values of pixels in a fundus color image captured by irradiating a fundus with a plurality of beams of single-color light having different wavelengths, the histogram being acquired for each channel corresponding to each beam of single-color light, a histogram correction step of acquiring a corrected histogram by correcting the histogram of each channel acquired in the histogram acquisition step, of which a target pattern is set for each channel in advance, so as to fit to the corresponding target pattern, and a color tone corrected image generation step of generating a color tone corrected image, in which a distribution of gradation values for each channel is represented by the corrected histogram, based on the corrected histogram of each channel.

13 Claims, 5 Drawing Sheets

(51) Int. Cl.
*G06T 5/40* (2006.01)
*G06T 7/44* (2017.01)
*G06T 11/00* (2006.01)
*H04N 1/60* (2006.01)

(52) U.S. Cl.
CPC .......... *H04N 1/6027* (2013.01); *G06T 11/001* (2013.01); *G06T 2207/10024* (2013.01)

(58) Field of Classification Search
CPC ...... H04N 1/6041; H04N 1/6058; H04N 5/57; H04N 9/64; H04N 9/73; H04N 9/77; H04N 1/6075; H04N 1/6077; H04N 9/643; H04N 9/646; G06T 7/44; G06T 5/40; G06T 11/001; G06T 2207/10024; G09G 5/02; G09G 5/10; G09G 2320/0271; G09G 2320/0276; G09G 2320/066

See application file for complete search history.

(56) References Cited

U.S. PATENT DOCUMENTS

| 2005/0134796 | A1 | | 6/2005 | Zelvin et al. |
| 2013/0028484 | A1 | * | 1/2013 | Wada ..................... A61B 3/12 382/128 |
| 2016/0220108 | A1 | | 8/2016 | Ono |

FOREIGN PATENT DOCUMENTS

| JP | 2010-512878 | A | | 4/2010 | |
| JP | 2011151653 | A | * | 8/2011 | ............... G06T 5/40 |
| JP | 2016-59539 | A | | 4/2016 | |
| JP | 2016-140428 | A | | 8/2016 | |

* cited by examiner

OPHTHALMOLOGIC IMAGE PROCESSING METHOD AND FUNDUS IMAGING APPARATUS

STATEMENT REGARDING PRIOR DISCLOSURES BY THE INVENTORS

The inventors of the present application disclosed the subject matter of the present application on Apr. 29, 2018 in "ARVO Annual Meeting 2018" held at the Hawaii Convention Center.

CROSS-REFERENCE TO RELATED APPLICATION

This application claims priority from Japanese Patent Application No. 2018-185472 filed on Sep. 28, 2018, the entire subject-matter of which is incorporated herein by reference.

TECHNICAL FIELD

The present disclosure relates to an ophthalmologic image processing method and a fundus imaging apparatus that processes a fundus image of a subject eye captured with using a plurality of beams of single-color light having different wavelengths.

BACKGROUND

As a fundus imaging apparatus which uses visible light to capture an image of a fundus of a subject eye, it is known not only an apparatus using white light as illumination light but also an apparatus using a plurality of beams of single-color light having different wavelengths as the illumination light.

A confocal type apparatus is known as the apparatus using a beam of single-color light as the illumination light. For example, JP-A-2016-059539 discloses an SLO apparatus in which laser light of four colors in the infrared range, red, blue, and green is emitted from a light source simultaneously or selectively, and a fundus image is generated based on fundus reflection light of each color light.

However, when a beam of single-color light is used as illumination light, differences of the reflection characteristics of individual fundus are emphasized in the fundus image as differences in color tone compared to a case where multi-color light (for example, white light) is used as the illumination light. In other words, when the beam of single-color light is used as the illumination light, a significant difference in color tone in the fundus image is likely to occur for every time imaging the subject eye.

In addition, in the confocal type apparatus as disclosed in JP-A-2016-059539, an alignment deviation and a focus deviation at the time of imaging are likely to affect the color tone.

SUMMARY

An object of the present disclosure is to suppress the difference in color tone for each fundus image.

There is provided an ophthalmologic image processing method including:

an imaging step of irradiating a fundus with a plurality of beams of single-color light having different wavelengths to capture a fundus color image based on fundus reflection light of the plurality of beams of single-color light, the imaging steps is performed in a fundus imaging apparatus; and a color tone corrected image generation step of generating a color tone corrected image with using a computer by correcting a gradation value of each pixel in the fundus color image such that a feature value for each channel corresponding to the beam of single-color light, which is based on a distribution of gradation values of pixels in the fundus color image, fits to a feature value in a target pattern predetermined for each channel.

There is provided an ophthalmologic image processing method including:

an imaging step of irradiating a fundus with a plurality of beams of single-color light having different wavelengths to capture a fundus color image based on fundus reflection light of the plurality of beams of single-color light, the imaging steps is performed in a fundus imaging apparatus; and a color tone corrected image generation step of generating a color tone corrected image with using a computer by correcting a gradation value of each pixel in the fundus color image such that a histogram for each channel corresponding to the beam of single-color light, which is based on a distribution of gradation values of pixels in the fundus color image, fits to a histogram in a target pattern predetermined for each channel.

There is provided a fundus imaging apparatus including:

an irradiation optical system configured to irradiate a fundus with a plurality of beams of single-color light having different wavelengths;

a light receiving optical system including a light receiving element configured to receive fundus reflection light of the plurality of beams of single-color light; and an image processing unit configured to generate a fundus color image based on a signal from the light receiving element, in which the image processing unit generates a color tone corrected image by correcting a gradation value of each pixel in the fundus color image such that a feature value for each channel corresponding to the beam of single-color light, which is based on a distribution of gradation values of pixels in the fundus color image, fits to a feature value in a target pattern predetermined for each channel.

According to the present disclosure, it is possible to suppress the difference in color tone for each fundus image.

DETAILED DESCRIPTION

[Summary]

Hereinafter, the present disclosure will be described based on an embodiment. For convenience, in the following description, unless otherwise noted, a processing content of an "ophthalmologic image processing program" according to the embodiment and an "ophthalmologic image processing method" will be described as being executed by a "fundus imaging apparatus".

<Overall Configuration>

A fundus imaging apparatus 1 (hereinafter, abbreviated as "the present apparatus 1") according to the embodiment includes at least an imaging optical system (10, 20) and an image processor 80. By having the image processor 80, the present apparatus 1 becomes a computer that performs various image processing. A processor that performs overall controls of operation of the apparatus may be co-used as the image processor 80. The image processor 80 may be separated from the processor that performs overall control of operation of the apparatus. In a memory to which the processor of processor 80 can access, an ophthalmologic image processing program may be stored.

Figure 1:
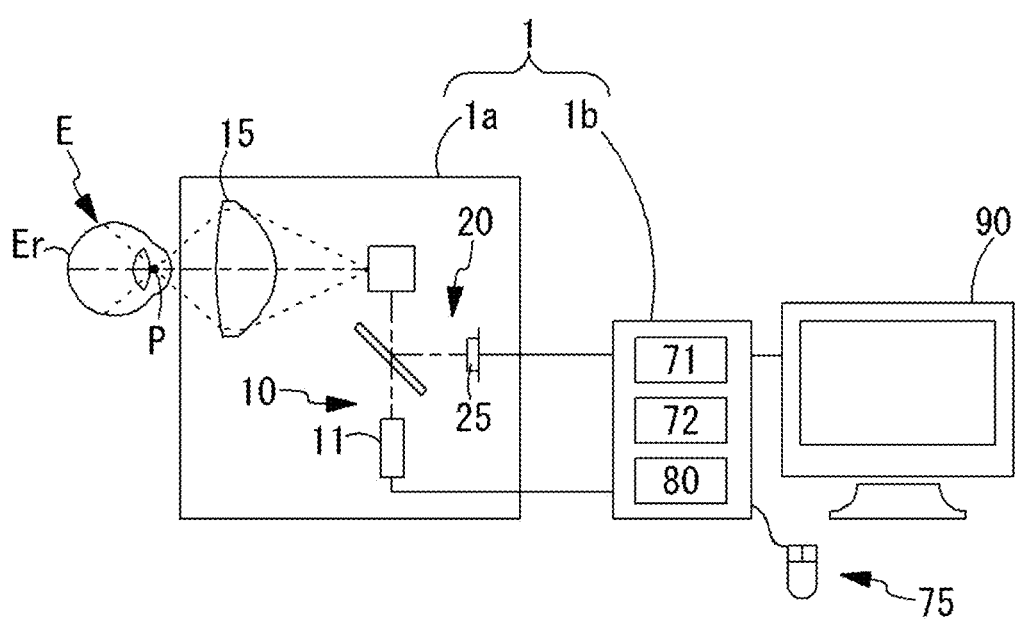
FIG. 1 is a diagram illustrating a schematic configuration of a fundus imaging apparatus according to an embodiment.

For example, as illustrated in FIG. 1, the present apparatus 1 is roughly divided into an optical unit 1a and a control unit 1b, and the imaging optical system (10, 20) may be stored in the optical unit 1a, and the image processor 80 may be stored in the control unit 1b, respectively. The control unit 1b includes various memories 72 in addition to a processor (CPU) 71. The ophthalmologic image processing program may be stored in the memory 72. In addition, an operation unit 75 (user interface) may be connected to the control unit 1b. The operation unit 75 may be a pointing device such as a mouse and a touch panel, or may be another user interface. For example, a PC may be used as the control unit 1b.

In addition, the present apparatus 1 may include a monitor 90. For example, the captured fundus image is displayed on the monitor 90. In addition, various GUIs may be displayed on the monitor 90.

<Imaging Optical System>

The imaging optical system (10, 20) images at least a fundus color image which is a kind of fundus image. In the present embodiment, the fundus image is a front image of the fundus. In addition, in the fundus color image, each pixel has color information. The imaging optical system (10, 20) includes an irradiation optical system 10 and a light receiving optical system 20 (refer to FIG. 1). Additionally, the imaging optical system (10, 20) may image the monochrome fundus images.

The irradiation optical system 10 irradiates the fundus with a plurality of beams of single-color light having different wavelengths. The light receiving optical system 20 includes at least a light receiving element 25 that receives fundus reflection light of a plurality of a beams of single-color light. A signal from the light receiving element 25 is input to the image processor 80, and as a result, the fundus color image is generated by the image processor 80. In the light receiving optical system 20, a plurality of light receiving elements 25 may be provided for each wavelength of a beam of single-color light. In this case, a plurality of beams of fundus reflection light having different wavelengths and a plurality of beams of single-color light fundus reflection light may be received simultaneously by a plurality of light receiving elements 25. In addition, a plurality of beams of fundus reflection light having different wavelengths may be received by one light receiving element 25 in a time division basis (in other words, at mutually different timings). As the light receiving element 25, any of a point light receiving element, a one-dimensional imaging device (line sensor), a two-dimensional imaging device, and the like may be used. Which one is adopted is appropriately selected according to the imaging method.

The irradiation optical system 10 may have a light source 11 for each wavelength. For example, as the light source 11, any one of a single color LED and various light sources such as a laser light source may be used. Here, the "beam of single-color light" has a narrow meaning that the light which cannot be spectrally resolved, but the present disclosure is not necessarily limited thereto. The "beam of single-color light" in the present disclosure may have a width of wavelength distribution that can be treated as a specific single color in the technical field of fundus imaging apparatus. However, the width of the wavelength distribution in the beam of single-color light is narrow enough to be clearly distinguishable from the white light in the technical field of the fundus imaging apparatus.

For example, the imaging optical system (10, 20) may irradiate the fundus with three colors of R (red), G (green) and B (blue) when capturing the fundus color image. At this time, the imaging optical systems 10 and 20 may irradiate the fundus with IR (infrared) light in addition to the three colors or may irradiate the fundus with the IR (infrared) light as a substitute for the R light. Here, when capturing the fundus color image, the fundus is radiated with three to four colors of light, but not necessarily limited thereto. The fundus may be radiated with two colors or five or more colors. In addition, the color combination described above is only an example, and the fundus color image may be captured with using another color combinations.

The imaging optical system (10, 20) may be a confocal optical system. In a case of the confocal optical system, the irradiation optical system 10 includes an optical scanner and causes the illumination light (here, the beam of single-color light) to be focused on the fundus in a point shape or line shape, and causes the illumination light to be scanned on the fundus by the light scanner. In addition, in the light receiving optical system 20, a harmful light removal unit (for example, a pinhole and a slit aperture, and the like) is provided at a fundus conjugate position. The harmful light removal unit guides the fundus reflection light from the area to which the illumination light is radiated, to the light receiving element 25, and removes the other light. Then, as a result of sequential light reception by the light receiving element 25, the front image of the fundus is acquired. In the line scan method, the light receiving element 25 may also be used as the harmful light removal unit. In this case, a line sensor used as the light receiving element 25 is disposed at the fundus conjugate position. An example of a non-confocal type imaging optical system includes an optical system of a general fundus camera. For more details of the confocal optical system, refer to, for example, JP-A-2016-059539 applied by the present applicant. This literature discloses a scanning laser ophthalmoscope which is an example of a fundus imaging apparatus having the confocal optical system.

<Image Processor>

As described above, the image processor 80 generates a fundus image based on a signal from the light receiving element 25. In the present embodiment, at least a fundus color image is generated as the fundus image. However, not necessarily limited thereto, the image processor 80 may additionally generate a monochrome fundus image based on the signal from the light receiving element 25.

Figure 2:
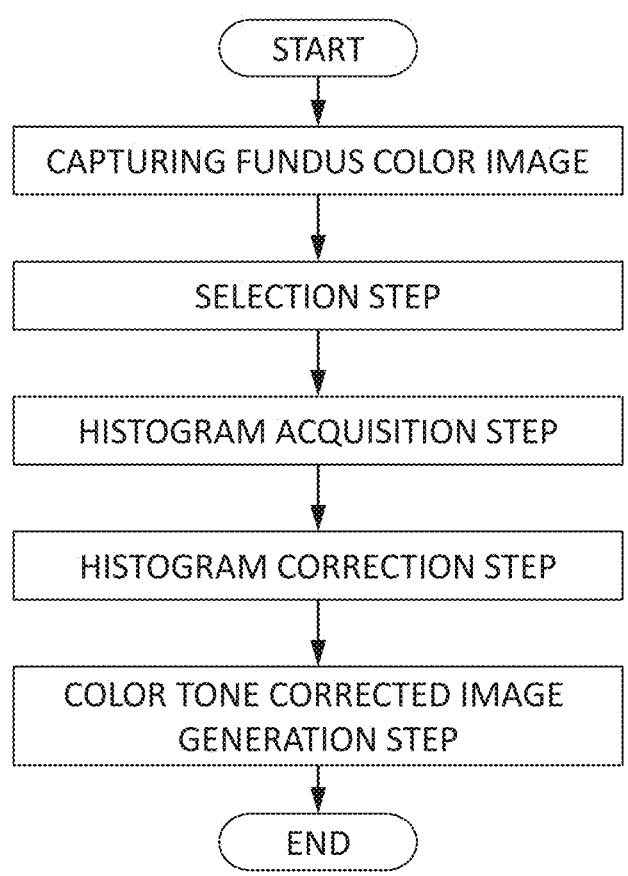
FIG. 2 is a flowchart illustrating an ophthalmologic image processing method according to the present embodiment.

In the present embodiment, the image processor 80 generates the fundus color image (in the present embodiment, referred to as a "color tone corrected image") expressed in a predetermined color tone regardless of the subject eye and the imaging conditions. This method will be described with reference to FIG. 2. Before performing each step, it is assumed that the fundus color image is captured by irradiating the fundus with a plurality of beams of single-color light having different wavelengths.

<Histogram Acquisition Step>

The image processor 80 performs a histogram acquisition step under a state in which the color fundus image is acquired in advance. In the histogram acquisition step, the image processor 80 acquires a histogram in the fundus color image (for convenience, referred to as "base image") to be corrected. The histogram represents the distribution of gradation values of pixels in the fundus color image. The histogram is acquired for each channel corresponding to each beam of single-color light. For example, the histograms in the R, G. and B channels of the base image may be respectively acquired by the image processor 80. In the following description, it is assumed that the acquired histogram has a population of all the pixels configuring the base image unless otherwise specified. However, not necessarily limited to this, and the pixels configuring a partial region in the base image may be a population.

It is preferable that a beam of single-color light is associated with one channel, but the correspondence relationship is not necessarily limited thereto. If the beam of single-color light has four or more colors, at least one channel may correspond to a multiple colored beams of single-color light. For example, if the base image is captured by irradiating the fundus with the four colors of IR, R, G, and B, the correspondence relationship may be defined such that two beams of single-color light of IR and R correspond to one channel (R channel) and the remaining two colors correspond to another channels, respectively. In addition, if the beam of single-color light has two colors, at least one color may correspond to two or more channels.

<Histogram Correction Step>

Subsequently, the image processor 80 performs a histogram correction step (histogram correction processing). In this step, the histogram of each channel acquired in the histogram acquisition step is corrected based on the target pattern. For convenience, the histogram corrected in the histogram correction step is referred to as a "corrected histogram". The target pattern is set in advance for each channel. The target pattern is information defining the targeted distribution of gradation values. The target pattern may be defined by the feature values in the targeted distribution of gradation values. For example, in the target pattern, at least two target values of a brightness (brightness) and a contrast may be defined. Various information can be used as the information that defines the target value of the brightness and the contrast. For example, the target value of the brightness may be any value of an average value, a median value, and a most frequent value of the tone values in the targeted distribution of gradation. In addition, the information defining the contrast may be any value of a standard deviation, a variance, and a half width in the targeted distribution of gradation. Specific examples of the target pattern will be described later.

In the histogram correction step, the image processor 80 corrects the histogram of each channel acquired in the histogram acquisition step so as to fit to the target pattern corresponding to each channel. In this way, the corrected histogram is obtained. The histogram of each channel may be corrected by, for example, linear processing. That is, addition, subtraction, multiplication, or division is appropriately performed on the gradation value of each pixel according to the difference between the histogram before the correction and the target pattern, and then, a corrected histogram may be obtained as a result thereof. In addition to or instead of the linear correction processing, the histogram may be corrected by non-linear processing. For example, each histogram may be corrected using a tone curve.

As a result of the above-described correction processing, the brightness and the contrast of each channel can approach the target pattern.

<Color Tone Corrected Image Generation Step>

The image processor 80 performs a color tone corrected image generation step to generate a color tone corrected image based on the corrected histogram of each channel. The color tone corrected image is a fundus color image in which the distribution of gradation values of each channel is represented by the corrected histogram. In other words, the color tone corrected image is expressed by a color tone which is corrected for the fundus color image that is based on the histogram before the correction, and which is a targeted color tone set in advance and is corresponding to the target pattern of each channel.

Here, when imaging with using the beam of single-color light as illumination light, the histogram of each channel is largely affected by individual differences in the reflection characteristics from the fundus (for example, depending on the presence or absence of a lesion, race, and the like), and thus, the color tone tends to have variations for each imaging. On the contrary, in the present embodiment, since the histogram of each channel is corrected so as to approach the target pattern regardless of the individual differences in the reflection characteristics, it is possible to suppress the color tone variations in the color tone corrected image for each imaging.

In addition, when the imaging optical system is confocal type, the imaging conditions such as alignment and focus are also likely to affect the histogram of each channel, and errors in imaging conditions for each imaging are likely to occur as the variations of the histogram for each imaging. That is, even when imaging a specific subject eye, it is difficult to stabilize the color tone in each imaging. On the other hand, as described above, in the color tone corrected image, the variations of color tone for each imaging is suppressed. For this reason, it can be considered that the above-described processing is particularly useful when the imaging is performed by a confocal type imaging optical system.

The color tone in the fundus color image may be considered to be corrected by hardware adjustment. For example, the output power of the light source 11, the gain of the light receiving element 25, and the like may be adjusted. However, the hardware does not necessarily have a sufficient adjustment range. In addition, for example, when the imaging optical system is confocal type, the choices of hardware are limited because relatively large adjustments are required. On the other hand, in the present embodiment, since the color tone is corrected by software, there are few hardware restrictions, which is advantageous.

In addition, a time-related deterioration in the output power of the light source 11 may be considered to change the color tone in the fundus color image, but the color tone corrected image is also valid for this point.

Specific Example of Target Pattern

Examples (a first pattern and a second pattern) of the target pattern that can be used in the histogram correction step will be described.

<First Pattern>

The first pattern represents the pattern of histogram of each channel (each channel of R, G and B) in the fundus color image captured by irradiating the fundus with the white light. The first pattern may be defined by the feature values (any one of the average value, the median value, and the most frequent value of the gradation value in the distribution of gradation, and any one of the standard deviation, the variance, and the half width in the distribution of gradation) in the histogram of the fundus color image captured with using the white light. These feature values are used as the target values for the correction in the histogram correction step. The first pattern may be determined based on, for example, the histogram of one fundus color image or may be determined based on the average histogram of a plurality of fundus color images. As the light source for emitting the white light, any one of a xenon lamp or a white LED may be used. The fundus color image may be, for example, a fundus camera image captured by a fundus camera.

Here, referring to FIG. 3, the features in the color tone corrected image in which the color tone is corrected by applying the first pattern will be described in detail. Each graph in FIG. 3 illustrates the histogram of each channel (each of R, G, and B channels) (the same applies to FIG. 4).

Figure 3:
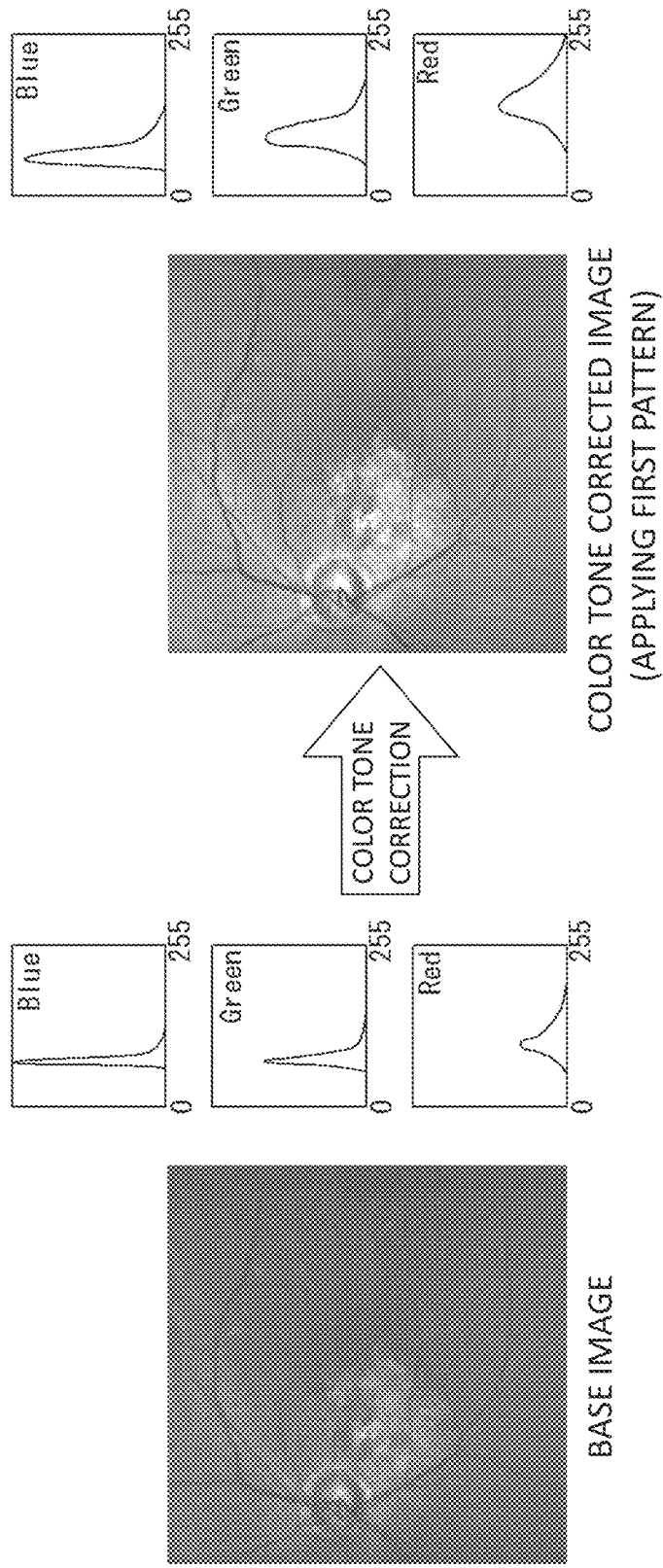
FIG. 3 is a diagram for explaining a color tone correction method, and illustrates the fundus image before and after the correction and a histogram of each channel when a first pattern is used as a target pattern.

In the color tone corrected image illustrated in FIG. 3, the histogram of each channel is corrected so as to fit to the first pattern defined by the next target value. A vertical axis represents the brightness and the lateral axis represents the contrast in the histogram of each channel illustrated in FIG. 3.

[Target Value of Brightness (Average Value of the Distribution of Gradation)]
R: 122
G: 66
B: 32
[Target Value of Contrast (Standard Deviation)]
R: 40
G: 27.5
B: 16.6

However, each target value is a gradation value in 256 gradation as a unit.

These target values presented as an example are determined based on the fundus color image (more specifically, a fundus camera image) captured with using the white light.

In the fundus color image captured with using the white light, it is characterized that the features on the deeper side of the retina can be easily observed. In addition, the depth of each wavelength in the fundus has a relationship of [Deep←((IR) R G B→shallow].

Therefore, in the first pattern, as the target value of the brightness in the R channel, a value on the high brightness side with respect to the target value of each of G and B channels is adopted. In addition, as the target value of the brightness in the G channel, a value on the high brightness side with respect to the target value of the B channel is adopted.

In addition, as the target value of the contrast in the R channel, a value on the high contrast side with respect to the target value of each of the G and B channels is adopted. In addition, as the target value of the contrast in the G channel, a value on the high contrast side with respect to the target value of the B channel is adopted. From the color tone corrected image to which such the first pattern is applied, information on the deeper side of the fundus can be easily obtained similarly to the fundus color image captured with using the white light.

In addition, when the white light is used as the illumination light, the wavelength range of the illumination light for each channel is wide, and the influence of the reflection characteristics from the fundus is relatively reduced compared to a case when the beam of single-color light is used as the illumination light, and thus, the stable color tone can be obtained. On the other hand, when a fundus color image captured with using the beam of single-color light, the reflection characteristics from the fundus easily affects the color tone, and thus, it is difficult to stabilize the color tone. For example, from the histogram in the base image illustrated as an example in FIG. 3, it can be seen that there is no clear difference in the brightness and contrast between the G channel and the B channel, but the reproducibility of such color tone features is not high.

In addition, in the field of fundus examination, the color tone of the fundus color image captured with using the white light has been widely spread to examiner as a result of the fundus color image captured with using the white light being used for many years. Compared to this, it is hard to say that the color tone of the fundus color image captured with using the beam of single-color light is sufficiently spread to the examiner.

On the contrary, it is meaningful that the fundus color image captured with using the beam of single-color light can be expressed with a color tone familiar to the examiner by correcting the color tone using the first pattern.

<Second Pattern>

The second pattern is a target pattern for matching the distribution of gradation values between each channel. The term "matching" used herein does not have to be exact matching but may be substantial matching. In other words, the second pattern is a target pattern for suppressing the difference in distribution of gradation values between each channel.

Here, referring to FIG. 4, the features in the color tone corrected image in which the color tone is corrected by applying the second pattern will be described in detail.

Figure 4:
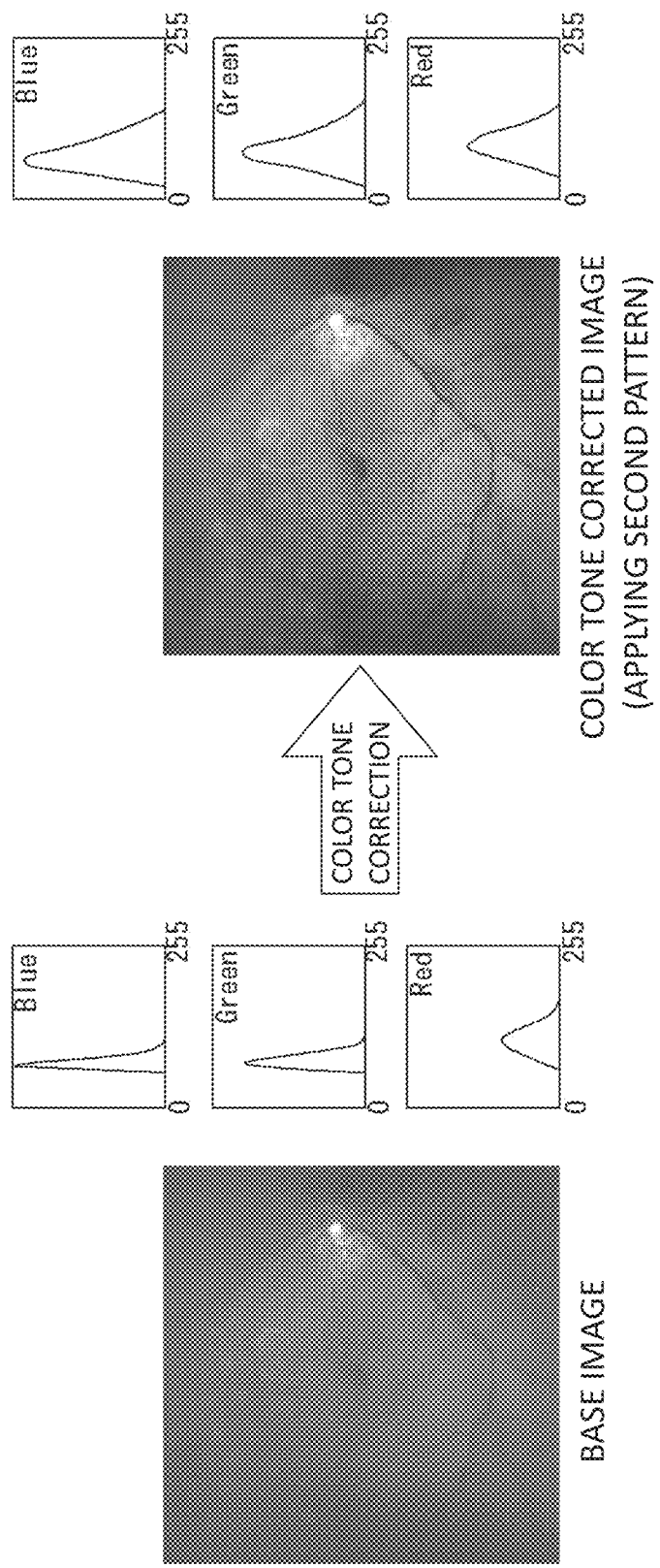
FIG. 4 is a diagram for explaining a color tone correction method, and illustrates the fundus image before and after the correction and a histogram of each channel when a second pattern is used as the target pattern.

In the color tone corrected image illustrated in FIG. 4, the histogram of each channel is corrected so as to fit to the second pattern defined by the next target value. A vertical axis represents the brightness and the lateral axis represents the contrast in the histogram of each channel illustrated in FIG. 4.

[Target Value of Brightness (Average Value of the Distribution of Gradation)]
R: 90.6
G: 79.8
B: 72.6
[Target Value of Contrast (Standard Deviation)]
R: 33.8
G: 29.8
B: 28.3

In the first pattern described above, the target values of the contrast had relatively large errors between channels, however, as described above, the target values of the contrast in the second pattern substantially match each other around 30.

In addition, the target value of the brightness in the second pattern has an error of up to 20 between the channels, however, in the first pattern, since the error is about 90 maximum between the channels, compared to this, the error in the second pattern described above is sufficiently small.

As described above, in the color tone corrected image to which the second pattern is applied, since the target values of the brightness and contrast in each channel of R, G, and B substantially match between each channel, it is possible to evenly express the features of the retina from the surface side to the deep side. In addition, in the second pattern, the target value of the contrast in each of the G and B channels may be set to a large value with respect to the contrast of each of the G and B channels in the fundus color image captured with using white light. In this way, in the color tone corrected image to which the second pattern is applied, it becomes easier for the examiner to grasp the features of the surface side of the retina compared to a case when the first pattern is applied (that is, a case where the image is captured with using the white light). For example, in the color tone corrected image to which the second pattern is applied, new blood vessels generated in a nerve fiber layer (NFL) are more emphasized and expressed.

In addition, the second pattern is a pattern that increases at least one of the brightness and the contrast in the second channel (one or both of G and B channels: second channel in the present embodiment) such that the distribution of gradation of the other channel approaches the distribution of gradation of the R channel (first channel in the present embodiment) from which the high-contrast information can be easily obtained originally, and thus, it can also be said that the surface side of the retina can be easily expressed.

<Other Patterns>

In addition, the target pattern is not limited to the above-described two types. For example, a third pattern may be prepared as a target pattern to emphasize and express the features of the surface side of the retina compared to the deep side of the retina. In the third pattern, the target value of the contrast in the R channel may have a smaller value than at least the B channel (or each of the B and G channels). In this way, the features of the surface side of the retina are more easily emphasized and expressed.

In addition, a plurality of target patterns may be prepared for reproducing the color tone of the fundus color image in each race. In this case, the target pattern may be selected according to the race of the patient. If such a target pattern is applied, for example, a fundus color image can be expressed with a natural color tone according to race.

In addition, a target pattern for reproducing the color tone in a particular manufacturer's apparatus or in a particular product (as identified by model or product name) may be prepared. When such a target pattern is applied, it is easy to compare the fundus color images captured by apparatuses different for each other. In this case, it is considered that the angle of view of the fundus color image captured by the present apparatus 1 is different from the angle of view of an image obtained by another apparatus to which the target pattern is referred. As a specific example, when the angle of view of the present apparatus 1 is 60° while the angle of view of the fundus camera that is to try to reproduce the color tone is 30°, when trying to apply the color tone in an image with a field of view of 30° by a fundus camera to the entire image with a field of view of 60°, it may be a color tone in which the examiner feels uncomfortable. Therefore, in this case, after limiting the region where the histogram is acquired in the histogram acquisition step to the range of center 30°, and then, the correction amounts of the brightness and the contrast may be determined in the histogram correction step. However, the range of correction of the gradation value is not limited to the range of the center 30°, but may be the entire range of the angle of view 60°. In addition, conversely, if the angle of view of another apparatus referenced as the target pattern is larger than the angle of view of the present apparatus 1, the target pattern may be defined based on the distribution of gradation of a part of the entire image obtained by another apparatus.

<Selection of Target Pattern>

The image processor 80 may further perform a selection step. A plurality of target patterns are prepared for each channel, and, a target pattern to be used in the histogram correction processing is selected from them in the selection step. For example, the target pattern to be used may be selected between the first pattern and the second pattern described above. The target pattern to be used may be selected based on the examiner's operation. In this way, it possible to generate a fundus color image represented by the examiner's desired color tone.

Figure 5:
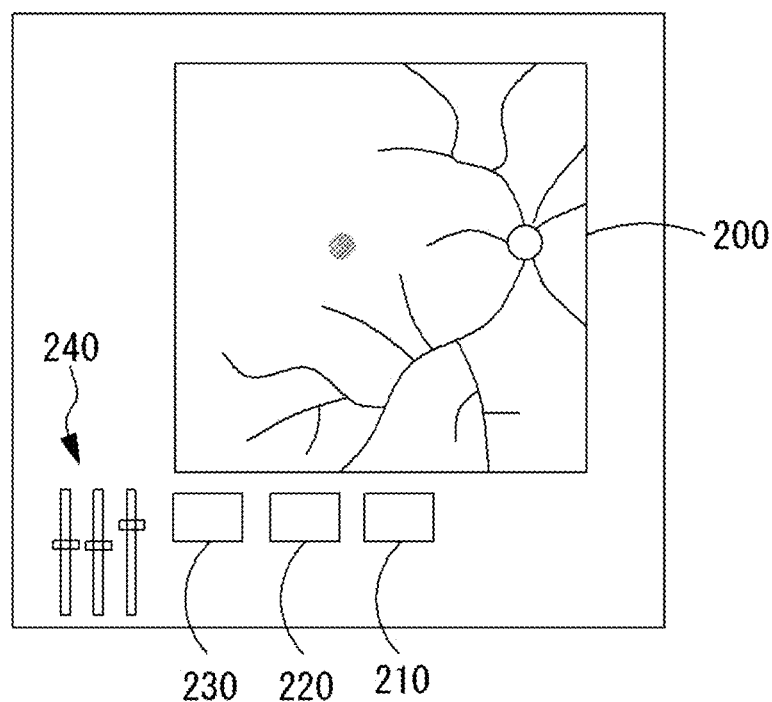
FIG. 5 is a diagram illustrating an example of a screen configuration.

For example, in order to cause the examiner to select the target pattern, a selection screen illustrated in FIG. 5 may be displayed on the monitor 90. On the selection screen, a GUI for receiving an operation for selecting the target pattern is displayed. As an example, in FIG. 5, pattern selection buttons 210 and 220 are displayed. In FIG. 5, two pattern selection buttons 210 and 220 are provided, and respectively correspond to the first pattern and the second pattern. On the selection screen, the fundus color image is displayed in the area 200 along with the selection buttons 210 and 220. By selecting any one of the two selection buttons 210 and 220 via the operation unit 75, a color tone corrected image is generated using the selected pattern and is displayed in the area 200.

Furthermore, a GUI may be provided on the selection screen for further manually adjusting the color tone in the fundus color image (the base image and the color tone corrected image) displayed on the selection screen. For example, in FIG. 5, a slider 240 for adjusting the brightness and the contrast of each channel is provided. The operation on the slider 240 is reflected in the fundus color image displayed in the area 200. In this way, it possible to observe the fundus color image represented by the examiner's desired color tone. The fundus color image of which the color tone is manually adjusted may be stored in the memory 72 based on a predetermined operation.

The target pattern after manual adjustment used for the color tone correction at this time may be able to be stored in the memory 72 as a new preset target pattern. The stored target pattern may be selectable in the selection screen together with the first pattern and the second pattern. The new target pattern to be stored is not limited to those generated as a result of adjustments with respect to other preset patterns (for example, the first pattern and the second pattern), but may have a combination of the brightness and the contrast designated by the examiner on a zero basis as a target value.

Furthermore, a reset button 230 may be provided on the selection screen. By operating the reset button 230, the fundus color image before correction is displayed in the area 200.

<Change Target Pattern According to Switching of Angle of View>

The imaging optical system (10, 20) may include an angle of view switching unit that changes the angle of view. For example, the angle of view switching unit may change the angle of view by switching the optical configuration of the objective optical system 15 included in the imaging optical system (10, 20). Specifically, the angle of view switching unit may include an insertion and removal mechanism for inserting and removing optical elements to and from the objective optical system 15. A lens, a mirror, a prism, and the like can be used as the optical elements. In addition, the angle of view switching unit may be a zoom mechanism in which the refractive state is changed by changing the positional relationship of two or more lenses along the optical path. In addition, a variable refraction lens such as a liquid crystal lens may be used as the angle of view switching unit.

At this time, the color tone in the fundus color image can be changed according to the angle of view. Therefore, the target pattern of each channel may be prepared for each angle of view. The image processor 80 may select the target pattern corresponding to the angle of view in the histogram correction step, and may correct the histogram in each channel using the selected target pattern. As a result thereof, the fundus color images having a suitable color tone for each angle of view can be acquired as the color tone corrected images.

As described above, the description is was made based on the embodiment, however, the contents of the embodiment can be appropriately changed when the present disclosure is embodied.

For example, in the embodiment described above, the base image is captured by irradiating the fundus with a plurality of beams of single-color light having different wavelengths. The base image may be captured as the fundus color image by irradiating the fundus with the white light for the correction processing using a target pattern. In this case, a certain effect to stabilize the color tone can be also obtained.

What is claimed is:

1. An ophthalmologic image processing method comprising: an imaging step of irradiating a fundus with a plurality of beams of single-color light having different wavelengths to capture a fundus color image based on fundus reflection light of the plurality of beams of single-color light, the imaging steps is performed in a fundus imaging apparatus, wherein the plurality of beams of single-color light correspond to a plurality of target patterns associated with color channels; and a color tone corrected image generation step of generating a color tone corrected image with using a computer by correcting a gradation value of each pixel in the fundus color image such that a feature value for each channel corresponding to the beam of single-color light, which is based on a distribution of gradation values of pixels in the fundus color image, matches a feature value in a target pattern predetermined for each channel; and wherein a first pattern, which is a pattern of histogram of each channel in a fundus color image captured by irradiating a fundus with white light, is set as the target pattern in advance.

2. The ophthalmologic image processing method according to claim 1,
wherein the feature value is a value defining a histogram based on the distribution of gradation value of each pixel.

3. The ophthalmologic image processing method according to claim 2,
wherein the histogram has a population of pixels configuring a partial area in the fundus color image.

4. The ophthalmologic image processing method according to claim 1,
wherein the first pattern is a pattern of histogram in a fundus camera image captured by a fundus camera.

5. An ophthalmologic image processing method comprising: an imaging step of irradiating a fundus with a plurality of beams of single-color light having different wavelengths to capture a fundus color image based on fundus reflection light of the plurality of beams of single-color light, the imaging steps is performed in a fundus imaging apparatus, wherein the plurality of beams of single-color light correspond to a plurality of target patterns associated with color channels; and a color tone corrected image generation step of generating a color tone corrected image with using a computer by correcting a gradation value of each pixel in the fundus color image such that a feature value for each channel corresponding to the beam of single- color light, which is based on a distribution of gradation values of pixels in the fundus color image, matches a feature value in a target pattern predetermined for each channel; wherein the histogram has at least two types of channels including an R (Red) channel as a first channel, and at least one of a G (Green) channel and a B (Blue) channel as a second channel, and as a second pattern which is one of the target patterns, a pattern that increases at least one of a brightness and a contrast in the second channel is set in advance such that a distribution of gradation in the second channel approaches a distribution of gradation in the first channel.

6. The ophthalmologic image processing method according to claim 1,
wherein, as one of the target patterns, a second pattern for matching a distribution of gradation values between channels is set in advance.

7. The ophthalmologic image processing method according to claim 5, wherein the feature value is a value defining a histogram based on the distribution of gradation value of each pixel.

8. The ophthalmologic image processing method according to claim 7, wherein the histogram has a population of pixels configuring a partial area in the fundus color image.

9. The ophthalmologic image processing method according to claim 5, wherein, as one of the target patterns, a second pattern for matching a distribution of gradation values between channels is set in advance.

10. An ophthalmologic image processing method comprising: an imaging step of irradiating a fundus with a plurality of beams of single-color light having different wavelengths to capture a fundus color image based on fundus reflection light of the plurality of beams of single-color light, the imaging steps is performed in a fundus imaging apparatus, wherein the plurality of beams of single-color light correspond to a plurality of target patterns associated with color channels; a color tone corrected image generation step of generating a color tone corrected image with using a computer by correcting a gradation value of each pixel in the fundus color image such that a feature value for each channel corresponding to the beam of single-color light, which is based on a distribution of gradation values of pixels in the fundus color image, matches a feature value in a target pattern predetermined for each channel; a selection step of selecting the target pattern from a first pattern and a second pattern which are the target patterns being at least different from each other; wherein a GUI for receiving an operation for selecting the first pattern or the second pattern, and the fundus color image are simultaneously displayed on a monitor, and a color tone corrected image corrected by either of the first pattern and the second pattern is switched to be displayed according to the operation to the GUI.

11. The ophthalmologic image processing method according to claim 10, wherein the feature value is a value defining a histogram based on the distribution of gradation value of each pixel.

12. The ophthalmologic image processing method according to claim 11, wherein the histogram has a population of pixels configuring a partial area in the fundus color image.

13. The ophthalmologic image processing method according to claim 10, wherein, as one of the target patterns, a second pattern for matching a distribution of gradation values between channels is set in advance.

* * * * *